United States Patent
Hsiung et al.

(10) Patent No.: US 10,429,240 B2
(45) Date of Patent: Oct. 1, 2019

(54) TRANSFER OF A CALIBRATION MODEL USING A SPARSE TRANSFER SET

(71) Applicant: Viavi Solutions Inc., Milpitas, CA (US)

(72) Inventors: Changmeng Hsiung, Redwood City, CA (US); Lan Sun, Santa Rosa, CA (US); Christopher G. Pederson, Santa Rosa, CA (US)

(73) Assignee: VIAVI Solutions Inc., San Jose, CA (US)

( * ) Notice: Subject to any disclaimer, the term of this patent is extended or adjusted under 35 U.S.C. 154(b) by 156 days.

(21) Appl. No.: 15/614,110

(22) Filed: Jun. 5, 2017

(65) Prior Publication Data

US 2018/0031421 A1 Feb. 1, 2018

Related U.S. Application Data

(60) Provisional application No. 62/368,741, filed on Jul. 29, 2016.

(51) Int. Cl.
*G06F 11/30* (2006.01)
*G01J 3/28* (2006.01)
(Continued)

(52) U.S. Cl.
CPC ............ *G01J 3/28* (2013.01); *G01J 3/027* (2013.01); *G01J 3/0297* (2013.01);
(Continued)

(58) Field of Classification Search
CPC ........................................................ G01J 3/28
See application file for complete search history.

(56) References Cited

U.S. PATENT DOCUMENTS

2004/0033618 A1   2/2004   Haass et al.
2015/0160121 A1*  6/2015   Ridder ................ G01N 21/274
                                                              702/85

FOREIGN PATENT DOCUMENTS

WO        WO 01/84122 A2    11/2001

OTHER PUBLICATIONS

Ozdemir D et al.: "Multi-instrument calibration with genetic regresson in UV-Visible Spectroscopy" Applied Spectroscopy, the Society for Applied Spectroscopy, Baltimore, US, vol. 53, No. 2, Feb. 1, 1999 (Feb. 1, 1999), pp. 210-217, XP000822230, ISSN: 0003-7028, DOI: 10.1366/0003702991946343 (Year: 1999).*

(Continued)

*Primary Examiner* — Phuong Huynh
(74) *Attorney, Agent, or Firm* — Harrity & Harrity, LLP

(57) ABSTRACT

A device may obtain a master calibration set, associated with a master calibration model of a master instrument, that includes spectra, associated with a set of samples, generated by the master instrument. The device may identify a selected set of master calibrants based on the master calibration set. The device may obtain a selected set of target calibrants that includes spectra, associated with the subset of the set of samples, generated by the target instrument. The device may create a transfer set based on the selected set of master calibrants and the selected set of target calibrants. The device may create a target calibration set, corresponding to the master calibration set, based on the transfer set. The device may generate, using an optimization technique associated with the transfer set and a support vector regression modeling technique, a transferred calibration model, for the target instrument, based on the target calibration set.

20 Claims, 6 Drawing Sheets

(51) Int. Cl.
 G06F 17/50 (2006.01)
 G01J 3/02 (2006.01)
 G01N 21/27 (2006.01)
(52) U.S. Cl.
 CPC .......... *G01N 21/274* (2013.01); *G06F 17/50* (2013.01); *G01J 2003/2866* (2013.01); *G01J 2003/2873* (2013.01); *G01N 2201/127* (2013.01)

(56) References Cited

OTHER PUBLICATIONS

Extended European Search report corresponding to EP 17 18 3707, dated Dec. 5, 2017, 10 pages.
Barman et al., "Development of Robust Calibration Models using Support Vector Machines for Spectroscopic Monitoring of Blood Glucose", Analytical Chemistry, vol. 82, No. 23, Dec. 1, 2010, XP055428441, 8 pages.
Fernandex Pierna et al., "Combination of Support Vector Machines (SVM) and Near-Infrared (NIR) Imaging Spectroscopy for the Detection of Meat and Bone Meal (MBM) in Compound Feeds", Journal of Chemometrics, 2004, XP055330482, 10 pages.
Martins et al., "Multivariate Calibration Transfer Employing Variable Selection and Subagging", Journal of the Brazilian Chemical Society, vol. 21, No. 1, Jan. 2010, XP055428442, 8 pages.
Ozdemir et al., "Multi-instrument Calibration with Genetic Regression in UV-Visible Spectroscopy", Applied Spectroscopy, vol. 53, No. 2, Feb. 1999, XP000822230, 8 pages.
Balabin et al., "Support Vector Machine Regression (SVR/LS-SVM) an Alternative to Neural Networks (ANN) for analytical Chemistry? Comparison of Nonlinear Methods on Near Infrared (NIR) Spectroscopy Data", Analyst, vol. 136, No. 8, Jan. 2011, XP055428436, 10 pages.

\* cited by examiner

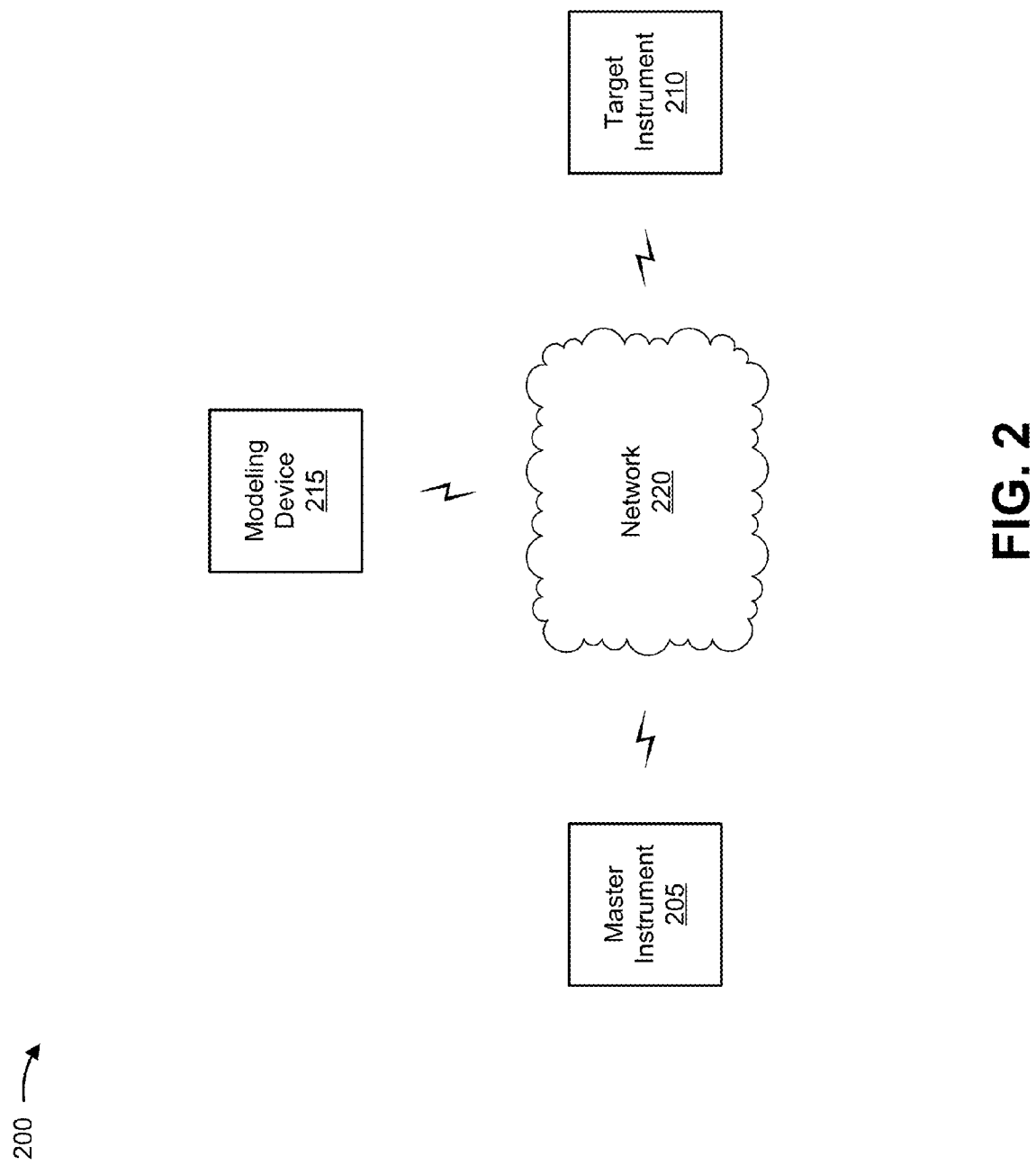

TRANSFER OF A CALIBRATION MODEL USING A SPARSE TRANSFER SET

RELATED APPLICATION

This application claims priority under 35 U.S.C. § 119 to U.S. Provisional Patent Application No. 62/368,741, filed on Jul. 29, 2016, the content of which is incorporated by reference herein in its entirety.

BACKGROUND

A spectroscopic instrument may be configured with a calibration model for calibrating spectroscopic measurements performed by the spectroscopic instrument. The calibration model is typically generated based on reference spectra, corresponding to known samples, and spectra, corresponding to the known samples, as measured by the spectroscopic instrument.

SUMMARY

According to some possible implementations, a device may include one or more processors to: obtain a master calibration set associated with a master calibration model of a master instrument, where the master calibration set may include spectra, associated with a set of samples, generated by the master instrument; identify a selected set of master calibrants based on the master calibration set, where the selected set of master calibrants may include spectra associated with a subset of the set of samples; obtain a selected set of target calibrants associated with a target instrument, where the selected set of target calibrants may include spectra, associated with the subset of the set of samples, generated by the target instrument; create a transfer set based on the selected set of master calibrants and the selected set of target calibrants, where the transfer set may be associated with the subset of the set of samples; create a target calibration set, corresponding to the master calibration set, based on the transfer set; and generate, based on a support vector regression modeling technique, a transferred calibration model, associated with the target instrument, based on the target calibration set, where the transferred calibration model may be generated using an optimization technique associated with the transfer set.

According to some possible implementations, a non-transitory computer-readable medium may store instructions that, when executed by one or more processors, cause the one or more processors to: obtain a master calibration set, associated with a master calibration model of a master instrument, that includes spectra associated with a set of samples, where the spectra may be generated by the master instrument based on scanning the set of samples; identify a selected set of master calibrants based on the master calibration set; obtain a selected set of target calibrants, associated with a target instrument, corresponding to the selected set of master calibrants; create a sparse transfer set based on the selected set of master calibrants and the selected set of target calibrants, where the sparse transfer set may be associated with five or fewer samples of the set of samples; generate a transfer matrix based on the sparse transfer set; create a target calibration set, corresponding to the master calibration set, using the transfer matrix; and generate a transferred calibration model, associated with the target instrument, based on the target calibration set, where the transferred calibration model may be generated using an optimization technique associated with the sparse transfer set.

According to some possible implementations, a method may include: obtaining, by a device, a first calibration set associated with a first calibration model of a first instrument, the first calibration set including spectra, associated with a set of samples, generated based on scans of the set of samples by the first instrument; identifying, by the device, a first selected set of calibrants of the first calibration set, where the first selected set of calibrants may correspond to a subset of the set of samples that includes five or fewer samples; obtaining, by the device, a second selected set of calibrants associated with a second instrument, where the second selected set of calibrants may include spectra, associated with the subset of samples, generated based on scans of the subset of samples by the second instrument; creating, by the device, a transfer set based on the first selected set of calibrants and the second selected set of calibrants, where the transfer set may correspond to the subset of samples; creating, by the device, a second calibration set, corresponding to the first calibration set, based on the transfer set; and generating, by the device and based on the second calibration set, a second calibration model associated with the second instrument, where the second calibration model may be generated based on a support vector regression modeling technique, and where the second calibration model may be generated using an optimization technique associated with the transfer set.

BRIEF DESCRIPTION OF THE DRAWINGS

FIG. 2 is a diagram of an example environment in which systems and/or methods, described herein, may be implemented;

DETAILED DESCRIPTION

Figure 1A:
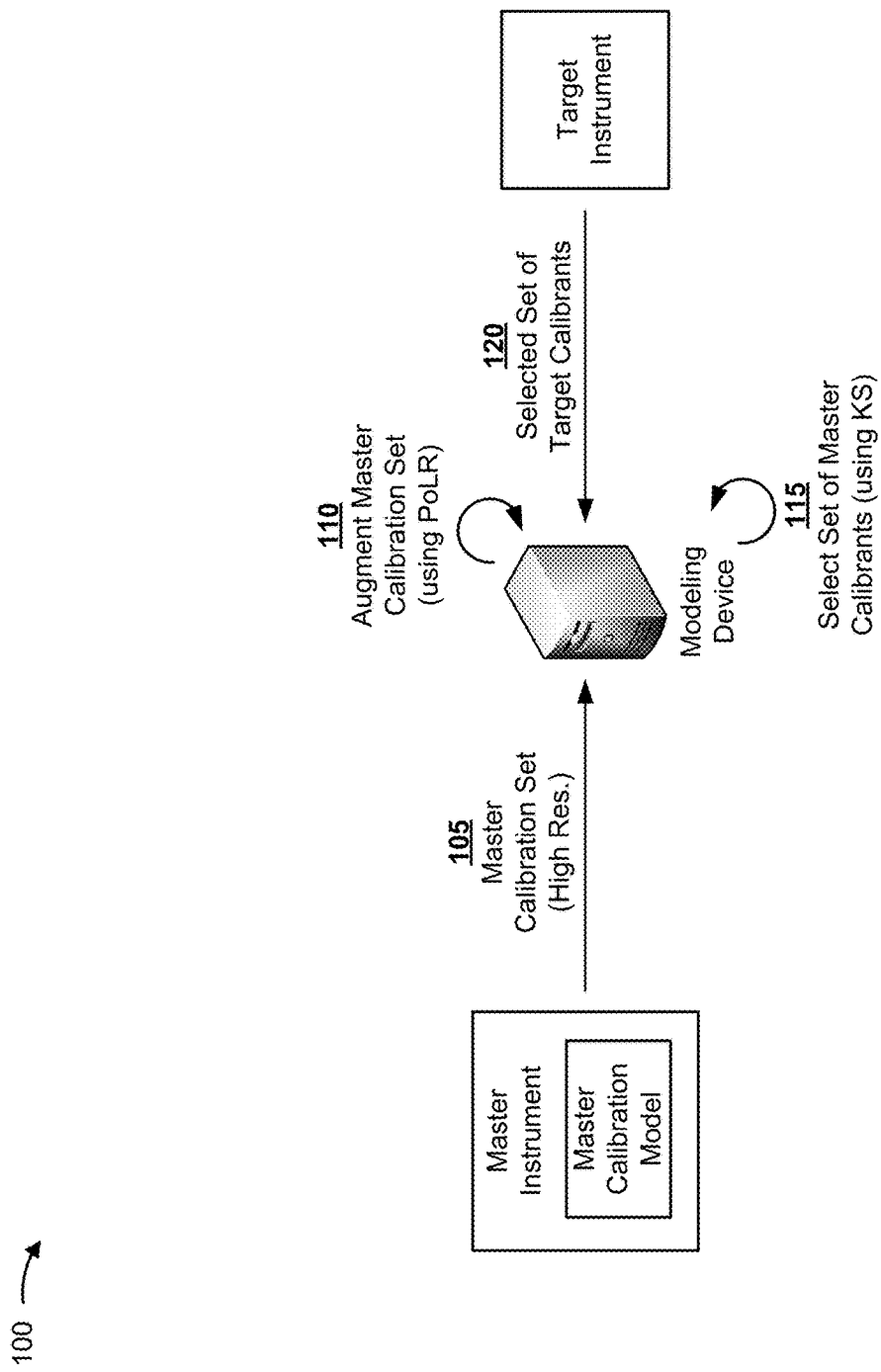
FIGS. 1A and 1B are diagrams of an overview of an example implementation described herein.

The following detailed description of example implementations refers to the accompanying drawings. The same reference numbers in different drawings may identify the same or similar elements.

A master spectroscopic instrument (herein referred to as a master instrument) may be configured with a master calibration model used to calibrate spectroscopic measurements of the master instrument. In some cases, a user may wish to transfer the master calibration model from the master instrument to a target spectroscopic instrument (herein referred to as a target instrument), such that the target instrument may be configured with a calibration model corresponding to the master calibration model. As an example, a user may wish to transfer a previously generated master calibration model, stored by a high-resolution master instrument, to a low-resolution target instrument.

However, since the master calibration model may be generated particularly for the master instrument, and the master instrument may differ from the target instrument (e.g., a high-resolution instrument designed for desktop use versus a low-resolution target instrument designed for handheld and/or mobile use), performance of the transferred calibration model (e.g., predictive accuracy) may be deteriorated as compared to the master calibration model. In some cases, such deterioration may be reduced when an increased number of calibrants (e.g., samples used for calibration) are included in a transfer set associated with transferring the master calibration model to the target instrument.

In such a case, the transferred calibration model is generated based on a greater amount of data (e.g., more spectral data may be used to generate the transferred calibration model due to the increased number of calibrants), which may lead to improved performance of the transferred calibration model as compared to a transferred calibration model generated based on spectral data associated with fewer calibrants. However, obtaining spectra for additional calibrants increases resource consumption (e.g., processing power, memory, battery usage, etc.) of the target instrument and/or the master instrument (e.g., since more spectral data needs to be collected), and also increases a burden on the users of the target instrument and/or the master instrument in order to generate spectra for the additional calibrants.

Implementations described herein provide techniques for improved transfer of a master calibration model from a master instrument to a target instrument, while allowing the master calibration model to be transferred to the target instrument using a sparse transfer set that includes spectra associated with a small number of calibrants (e.g., five or fewer). Implementations described herein also allow for transferring of a calibration model with improved model performance (e.g., as compared to a typical calibration model transfer).

Transfer of the master calibration model, as described herein, improves performance of the target instrument, reduces consumption of resources by the target instrument, and/or reduces a burden on a user of the target instrument (as compared to a typical manner of transferring the master calibration model). For example, transfer of the master calibration model, using the techniques described herein, may allow an improved and/or updated (e.g., newly generated and/or current) master calibration model to be efficiently and effectively disseminated to multiple target instruments, thereby improving predictive accuracy of the target instruments at a lower resource cost (e.g., battery power, processing resources, memory, network resources, man-hours, or the like) than the typical manner of transferring the master calibration model.

Moreover, transfer of the master calibration model, as described herein, allows the target instrument to be calibrated without a need for the target instrument to obtain spectral data for a high number of calibrants (e.g., more than five), thereby conserving usage of target instrument resources (e.g., battery power, processing resources, memory, or the like), while also reducing burden on a user of the target instrument (e.g., since less spectral data will need to be collected for generation of the transferred calibration model).

Additionally, transfer of the master calibration model, as described herein, allows the target instrument to be efficiently repaired and/or re-calibrated when, for example, the target instrument experiences a hardware error (e.g., a pixel defect), a spectral data collection issue (e.g., an unexpected spectral peak), or the like, thereby reducing down-time of the target instrument when such an error occurs.

Figure 1B:
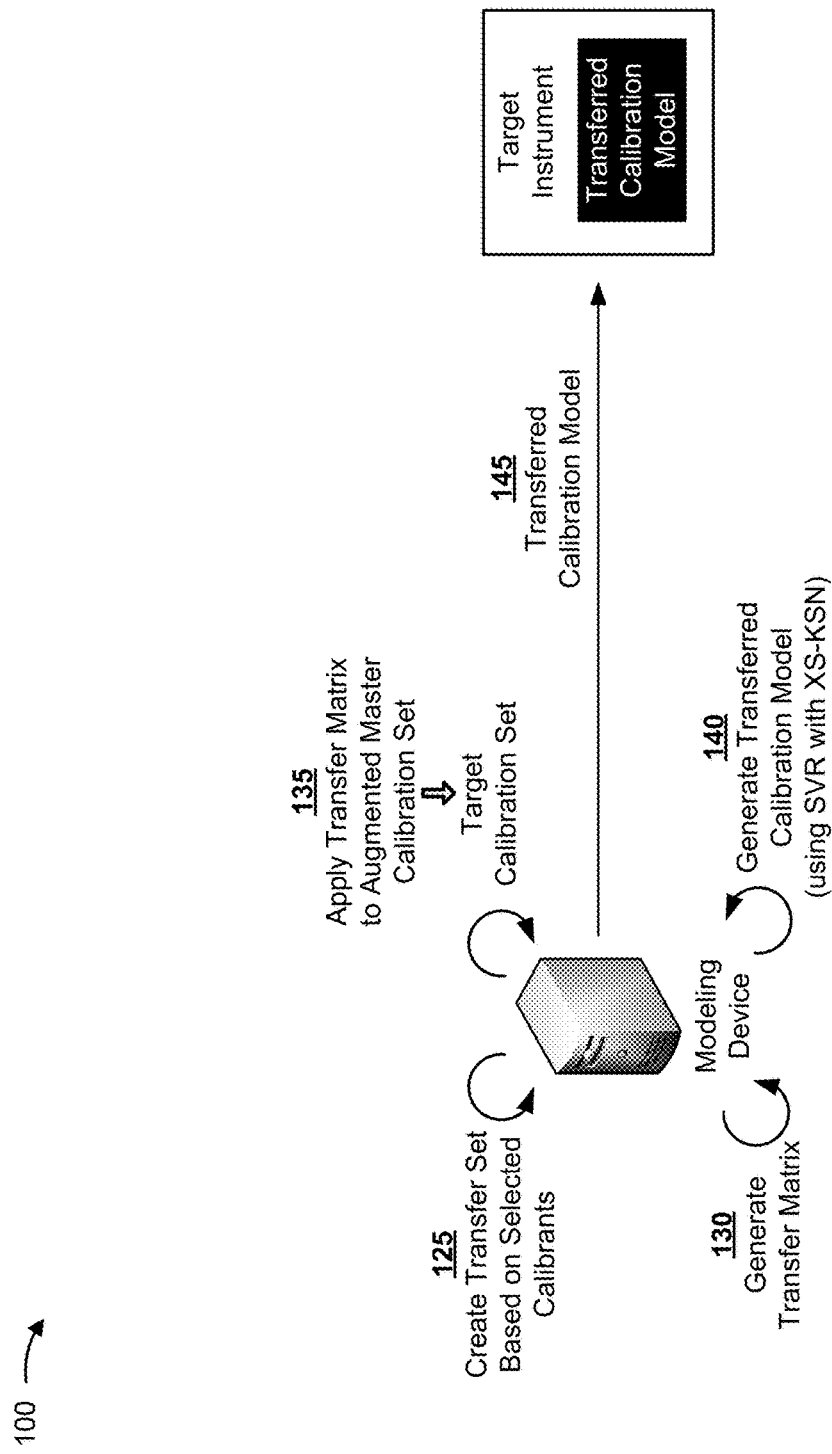

FIGS. 1A and 1B are diagrams of an overview of an example implementation 100 described herein. For the purposes of example implementation 100, assume that a master instrument stores a master calibration model associated with calibrating spectroscopic measurements of the master instrument. Further, assume that the master calibration model is to be transferred to a target instrument such that spectroscopic measurements of the target instrument may be calibrated.

As shown in FIG. 1A, and by reference number 105, a modeling device, associated with generating the transferred calibration model, may obtain, from the master instrument, a master calibration set associated with the master instrument. The master calibration set may include sets of spectra, associated with a set of samples, that are generated by the master instrument (e.g., based on spectral data, associated with the set of samples, collected by the master instrument). In some implementations, the master calibration set may be a basis on which the master calibration model is created. As noted in FIG. 1A, in some cases, the master calibration set may include high-resolution spectra generated by the master instrument.

As further shown in FIG. 1A, and by reference number 110, the modeling device may augment the master calibration set to create an augmented master calibration set. The augmented master calibration set may include a master calibration set that has been modified to include additional spectra for one or more samples associated with the master calibration set. In some implementations, the modeling device may augment the master calibration set in order to generate additional (e.g., low-resolution) spectra corresponding to the spectra included in the master calibration set. In some implementations, the modeling device may augment the master calibration set using a shifted grid interpolation technique that allows the modeling device to generate the additional spectra. As noted in FIG. 1A, the shifted grid interpolation technique may be referred to as a populated low-resolution (PoLR) technique. In some implementations, augmentation of the master calibration set may reduce bias associated with the transferred calibration model, as described below.

As further shown in FIG. 1A, and by reference number 115, the modeling device may select a set of master calibrants (e.g., from the augmented master calibration set, from a set of calibrant of a same type or same population as those included in the master calibration set). The selected set of master calibrants may include sets of spectra, corresponding to a set of samples included in the master calibration set, that are to be included in a transfer set associated with transferring the master calibration model from the master instrument to the target instrument. Here, the selected set of master calibrants may include a subset of the calibrants included in the master calibration set. For example, the selected set of master calibrants may include a small number of calibrants (e.g., five or fewer). In some implementations, the selected set of master calibrants is to be included in the transfer set associated with transferring the master calibration model.

In some implementations, the modeling device may select the set of master calibrants based on a Kennard-Stone (KS) algorithm. Use of a KS approach to select the set of master calibrants may result in a transferred calibration model with improved performance as compared to a transferred calibration model generated based on a set of master calibrants selected in a typical manner, as described below.

As further shown in FIG. 1A, and by reference number 120, the modeling device may obtain a selected set of target calibrants from the target instrument. The selected set of target calibrants may include sets of spectra, generated based on spectral data collected by the target instrument, that correspond to the samples associated with the selected set of master calibrants. In other words, the selected set of target calibrants may include spectra measured for a same set of samples as the spectra included in the selected set of master calibrants. In some implementations, the selected set of target calibrants is to be included in the transfer set associated with transferring the master calibration model.

As shown in FIG. 1B, and by reference number 125, the modeling device may create the transfer set based on the selected set of master calibrants and the selected set of target calibrants. The transfer set is a set of calibrants including the selected set of target calibrants and the selected set of master calibrants. In other words, the transfer set may include the spectra corresponding to the samples associated with both the selected set of master calibrants and the selected set of target calibrants (i.e., a combination of the spectra as measured by the master instrument and the target instrument).

In some implementations, the transfer set may be used to generate a transfer matrix that is to be applied to the augmented master calibration set to create a target calibration set. In some implementations, the modeling device may apply the transfer matrix to the master calibration set (e.g., when the modeling device does not augment the master calibration set). In some implementations, the modeling device may create the transfer set based on the selected set of target calibrants and the selected set of master calibrants. For example, for a given sample, the modeling device may match spectra, generated by the target instrument, to spectra generated by the master instrument. In some implementations, the transfer set may be a sparse transfer set (i.e., a transfer set associated with five or fewer calibrants). Here, use of the sparse transfer set may act to reduce consumption of target instrument resources and/or user burden (e.g., since fewer spectra need to be generated by the target instrument), as described below.

As further shown in FIG. 1B, and by reference number 130, the modeling device may generate the transfer matrix based on the transfer set. The transfer matrix may include information that identifies a manner in which the spectra, associated with the samples included in the master calibration set, may be manipulated in order to generate a target calibration set based on which the transferred calibration model may be created. In other words, the transfer matrix may include a matrix associated with mapping the augmented master calibration set (or the master calibration set when no augmentation is performed) to create the target calibration set. In some implementations, the modeling device may create the transfer matrix based on the transfer set.

In some implementations, the modeling device may generate the transfer matrix after applying a transfer scheme to the transfer set. For example, the modeling device may apply a generalized least squares (GLS) scheme to the transfer set, and may generate the transfer matrix after applying the GLS scheme to the transfer set.

As further shown in FIG. 1B, and by reference number 135, the modeling device may apply the transfer matrix to the augmented master calibration set in order to create a target calibration set. The target calibration set may include sets of spectra, corresponding to the samples associated with the augmented master calibration set, from which the transferred calibration model may be generated. In other words, the target calibration set may include sets of spectra, associated with the target instrument, that are mapped from sets of spectra, corresponding to the samples included in the master calibration set, based on the transfer matrix.

As further shown in FIG. 1B, and by reference number 140, the modeling device may generate the transferred calibration model based on the target calibration set. As described above, the transferred calibration model may include a model, to be used to calibrate measurements obtained by the target instrument, that is generated based on the master calibration model associated with the master instrument.

As noted in FIG. 1B, in some implementations, the modeling device may generate the transferred model based on applying a support vector regression (SVR) modeling technique (i.e., a support vector machine (SVM) for regression) to the target calibration set. Use of the SVR modeling technique may result in a transferred calibration model with improved performance as compared to a transferred model that is generated using a typical modeling technique, such as a partial least squares (PLS) modeling technique, as described below.

In some implementations, the modeling device may determine a value of a model parameter (e.g., a C parameter associated with the SVR modeling technique), associated with the transferred calibration model, based on the transfer set that is selected using the KS approach (noted in FIG. 1 as using SVR with XS-KSN). Determining the model parameter based on the KS-selected transfer set may result in a transferred calibration model with improved performance as compared to a transferred model for which a model parameter is identified in a typical manner, such as by using a cross validation technique, as described below.

As further shown in FIG. 1B, and by reference number 145, the modeling device may provide the transferred calibration model to the target instrument. Here, the target instrument may store the transferred calibration model for use in calibrating spectroscopic measurements collected by the target instrument.

In this way, transfer of a master calibration model from a master instrument to a target instrument may be improved, while allowing the master calibration model to be transferred to the target instrument using a sparse transfer set that includes spectra associated with a small number of calibrants (e.g., five or fewer). Further, the transferred calibration model may have improved model performance as compared to a typical calibration model transfer technique.

As indicated above, FIGS. 1A and 1B are provided merely as an example. Other examples are possible and may differ from what was described with regard to FIGS. 1A and 1B.

FIG. 2 is a diagram of an example environment 200 in which systems and/or methods, described herein, may be implemented. As shown in FIG. 2, environment 200 may include a master instrument 205, a target instrument 210, a modeling device 215, and a network 220. Devices of environment 200 may interconnect via wired connections, wireless connections, or a combination of wired and wireless connections.

Master instrument 205 includes a device, configured with a master calibration model, that is capable of performing a spectroscopic measurement on a sample. For example, master instrument 205 may include a desktop (i.e., non-handheld) spectrometer device that performs spectroscopy (e.g., vibrational spectroscopy, such as near infrared (NIR) spectroscopy, mid-infrared spectroscopy (mid-IR), Raman spectroscopy, or the like). In some implementations, master instrument 205 may be capable of obtaining spectroscopic measurements at a higher resolution than spectroscopic measurements obtained by target instrument 210 (i.e., master instrument 205 may be a high-resolution device, while target instrument 210 may be a low-resolution device). In some implementations, master instrument 205 may be configured with a master calibration model for calibrating spectroscopic measurements obtained by master instrument 205. In some implementations, master instrument 205 may receive information from and/or transmit information to another device in environment 200, such as modeling device 215.

Target instrument 210 includes a device capable of performing a spectroscopic measurement on a sample based on a target calibration model, where the target calibration model may be generated based on a master calibration model associated with master instrument 205. For example, target instrument 210 may include a mobile spectrometer device or a handheld spectrometer device that performs spectroscopy. In some implementations, target instrument 210 may be capable of obtaining spectroscopic measurements at a lower resolution than spectroscopic measurements obtained by master instrument 205. In some implementations, target instrument 210 may receive information from and/or transmit information to another device in environment 200, such as modeling device 215.

Modeling device 215 includes a device capable of generating a target calibration model, for target instrument 210, based on information associated with a master calibration model associated with master instrument 205. In other words, modeling device 215 may be capable of transferring the master calibration model from master instrument 205 to target instrument 210 using a sparse transfer set. For example, modeling device 215 may include a server, a group of servers, a computer, a cloud computing device, or the like. In some implementations, modeling device 215 may receive information from and/or transmit information to another device in environment 200, such as master instrument 205 and/or target instrument 210.

Network 220 includes one or more wired and/or wireless networks. For example, network 220 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2.

Furthermore, two or more devices shown in FIG. 2 may be implemented within a single device, or a single device shown in FIG. 2 may be implemented as multiple, distributed devices. For example, although master instrument 205 and modeling device 215 are described as being two separate devices, master instrument 205 and modeling device 215 may be implemented within a single device. As another example, target instrument 210 and modeling device 215 may be implemented within a single device. Additionally, or alternatively, a set of devices (e.g., one or more devices) of environment 200 may perform one or more functions described as being performed by another set of devices of environment 200.

Figure 3:
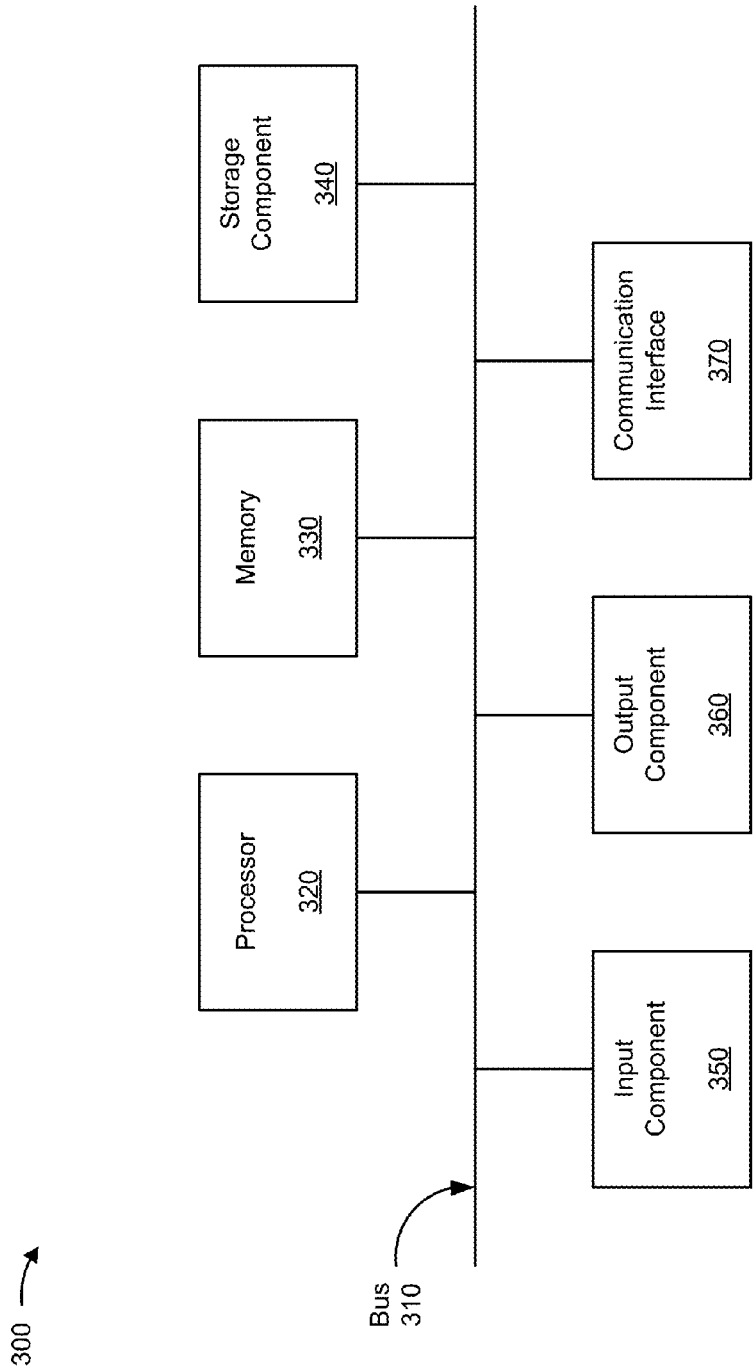
FIG. 3 is a diagram of example components of one or more devices of FIG. 2.

FIG. 3 is a diagram of example components of a device 300. Device 300 may correspond to master instrument 205, target instrument 210, and/or modeling device 215. In some implementations, master instrument 205, target instrument 210, and/or modeling device 215 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 includes a processor (e.g., a central processing unit (CPU), a graphics processing unit (GPU), and/or an accelerated processing unit (APU)), a microprocessor, a microcontroller, and/or any processing component (e.g., a field-programmable gate array (FPGA) and/or an application-specific integrated circuit (ASIC)) that interprets and/or executes instructions. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
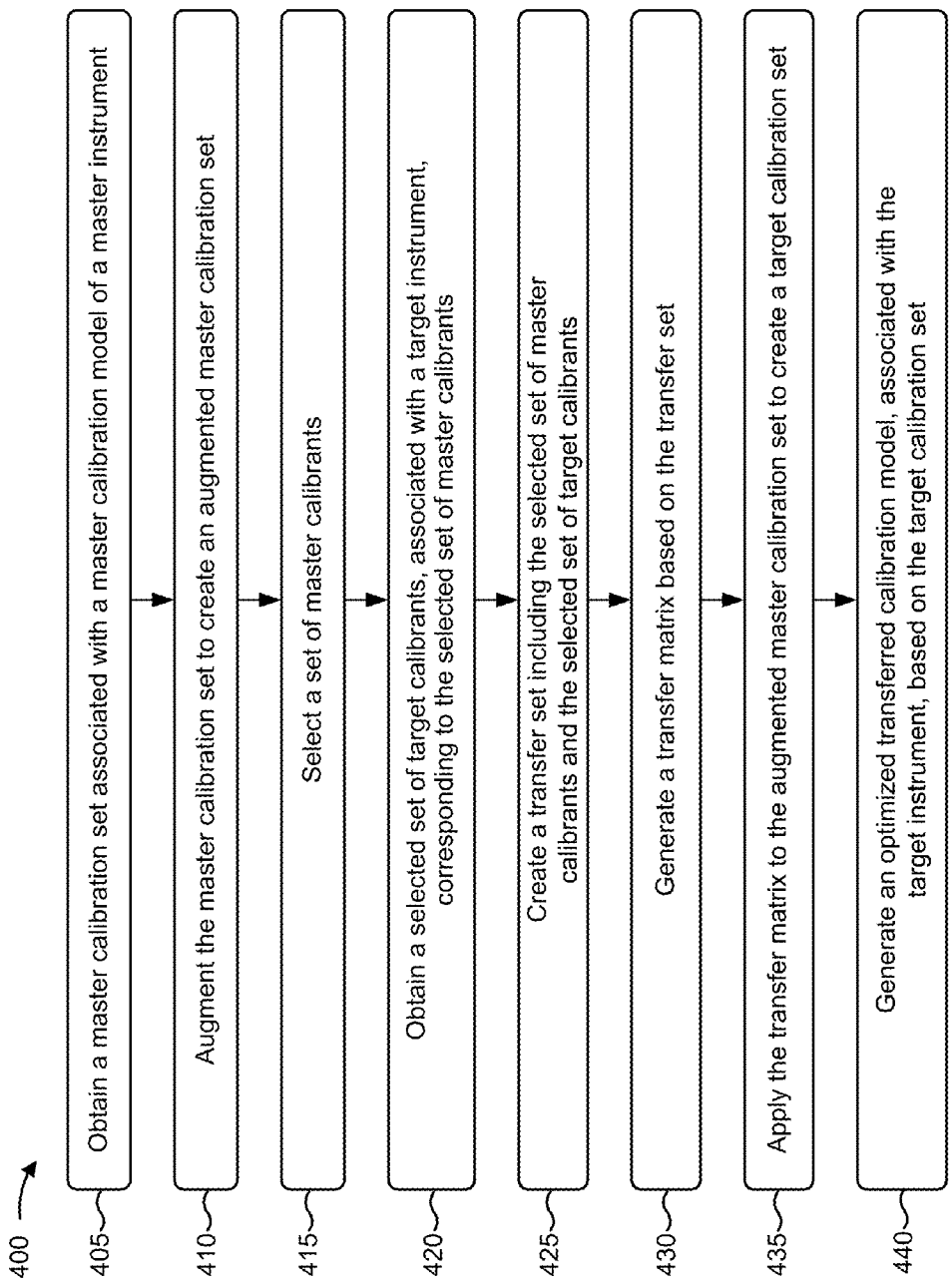
FIG. 4 is a flow chart of an example process for transferring a master calibration model from a master instrument to a target instrument using a sparse transfer set.

FIG. 4 is a flow chart of an example process 400 for transferring a master calibration model from master instrument 205 to target instrument 210 using a sparse transfer set. IN other words, FIG. 4 is a flow chart of an example process 400 for generating an optimized transferred calibration model (herein referred to as a transferred calibration model), associated with target instrument 210, based on a master calibration model associated with master instrument 205. In some implementations, one or more process blocks of FIG. 4 may be performed by modeling device 215. In some implementations, one or more process blocks of FIG. 4 may be performed by another device or a group of devices separate from or including modeling device 215, such as master instrument 205 and/or target instrument 210.

As shown in FIG. 4, process 400 may include obtaining a master calibration set associated with a master calibration model of a master instrument (block 405). For example, modeling device 215 may obtain a master calibration set associated with a master calibration model of master instrument 205. In some implementations, modeling device 215 may obtain the master calibration set when master instrument 205 provides the master calibration set. Additionally, or alternatively, modeling device 215 may obtain the master calibration set when modeling device 215 receives an indication that the master calibration model is to be transferred to target instrument 210 (i.e., that an optimized transferred calibration model, to be used by target instrument 210, is to be generated based on the master calibration model).

The master calibration set may include calibration spectra, associated with a set of samples, generated by master instrument 205 (e.g., based on spectral data collected by master instrument 205). Within the master calibration set, one or more calibration spectra may correspond to a given sample. In other words, the master calibration set may include sets of spectra generated based on measurements collected by master instrument 205, where each set of spectra is associated with a sample of the set of samples (e.g., one or more samples for which a characteristic, a property, and/or a classification is known). In some implementations, the master calibration set may be a basis on which a master calibration model, stored by master instrument 205, is created (e.g., such that spectroscopic measurements of master instrument 205 may be calibrated using the master calibration model).

In some implementations, a set of spectra, associated with a sample included in the master calibration set, may include a single spectrum. For example, the set of spectra may include one spectrum associated with the sample (e.g., a single spectrum generated based on spectral data collected during one scan of the sample by master instrument 205).

Additionally, or alternatively, a set of spectra, associated with a sample included in the master calibration set, may include multiple spectra. For example, the set of spectra may include multiple spectra associated with the sample (e.g., multiple spectra generated based on spectral data collected during multiple scans of the sample by master instrument 205). In some implementations, the master calibration set may include a first set of spectra that includes a single spectrum associated with a first sample, and a second set of spectra that includes multiple spectra associated with a second sample.

In some implementations, modeling device 215 may obtain the master calibration set from master instrument 205. For example, master instrument 205 may perform one or more scans on the one or more samples, may generate spectra associated with each sample based on spectral data collected during the one or more scans, may create the master calibration set based on the generated spectra, and may provide the master calibration set to modeling device 215. In some implementations, modeling device 215 may automatically receive the master calibration set. For example, master instrument 205 may be configured to automatically provide the master calibration set to modeling device 215 after the master calibration set is created. Additionally, or alternatively, modeling device 215 may obtain the master calibration set based on sending a request to master instrument 205 to provide the master calibration set. Additionally, or alternatively, modeling device 215 may obtain the master calibration set based on user input received by master instrument 205 and/or modeling device 215.

As further shown in FIG. 4, process 400 may include augmenting the master calibration set to create an augmented master calibration set (block 410). For example, modeling device 215 may augment the master calibration set to create an augmented master calibration set. In some implementations, modeling device 215 may augment the master calibration set to create the augmented master calibration set when modeling device 215 obtains the master calibration set from master instrument 205.

The augmented master calibration set may include a master calibration set that has been modified to include additional spectra associated with the samples included in the master calibration set. In some implementations, a set of master calibrants, associated with transferring the master calibration model, may be selected from the augmented master calibration set, as described below.

In some implementations, modeling device 215 may augment the master calibration set when a number of spectra, generated for a sample included in the master calibration set, satisfies a threshold (e.g., includes a single spectrum, includes two or fewer spectra, includes three or fewer spectra, includes fewer spectra than are collected by target instrument 210, etc.). For example, for a high-resolution master instrument 205, master instrument 205 may perform a single high-resolution scan of the one or more samples. Further, as described below, for a low-resolution target instrument 210, target instrument 210 may perform multiple low-resolution scans of the same one or more samples. In such a case, transferring the master calibration model based on a spectrum associated with the single high-resolution scan and the multiple spectra associated with the low-resolution scans may result in bias to the transferred calibration model, thereby negatively impacting predictive accuracy of the transferred calibration model (e.g., since the transferred calibration model is generated based on more spectra provided by target instrument 210 than provided by master instrument 205). Here, augmentation of the master calibration set may reduce bias in the transferred calibration model, thereby improving predictive accuracy of the transferred calibration model.

Additionally, modeling device 215 may augment the master calibration set in order to ensure that a number of spectra for each sample, that may be included in a transfer set associated with transferring the master calibration model, is the same for master instrument 205 and target instrument 210. Otherwise, in some implementations, modeling device 25 may be unable to transfer the master calibration model to target instrument 210 (e.g., when using a single spectra, associated with a sample, generated by master instrument 205 and multiple spectra, associated with the sample, generated by target instrument 210).

In some implementations, modeling device 215 may augment the master calibration set using a shifted grid interpolation technique. The shifted grid interpolation technique may allow modeling device 215 to generate additional spectra (herein referred to as replicates) based on a spectrum, associated with a sample, provided by master instrument 205. In some implementations, the shifted grid interpolation technique may be referred to as a PoLR technique.

Figure 5A:
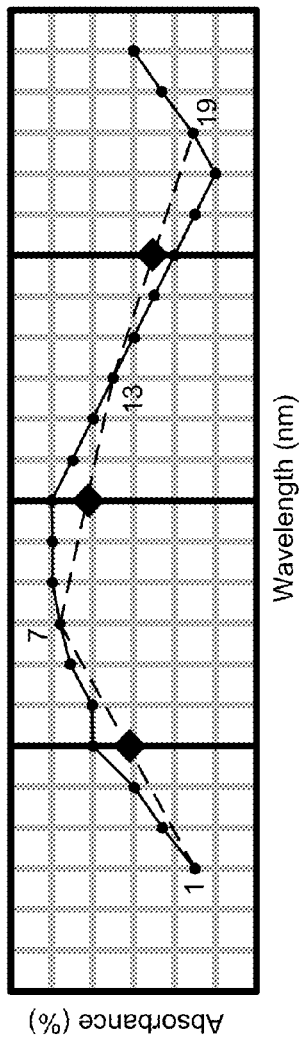
FIGS. 5A-5C are diagrams illustrating a manner in which a modeling device may perform shifted grid interpolation in order to augment a master calibration set associated with transferring a master calibration model.
Figure 5B:
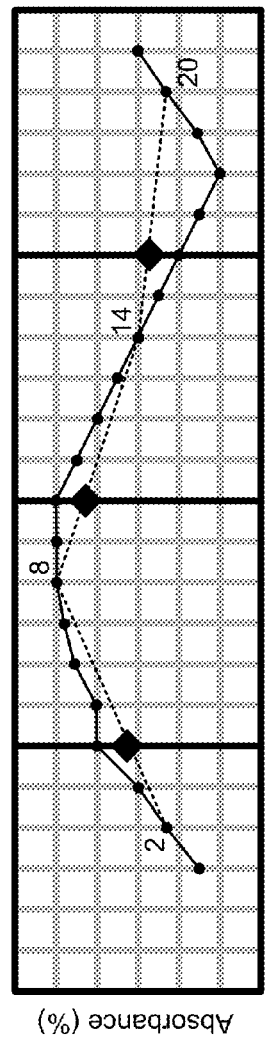
Figure 5C:
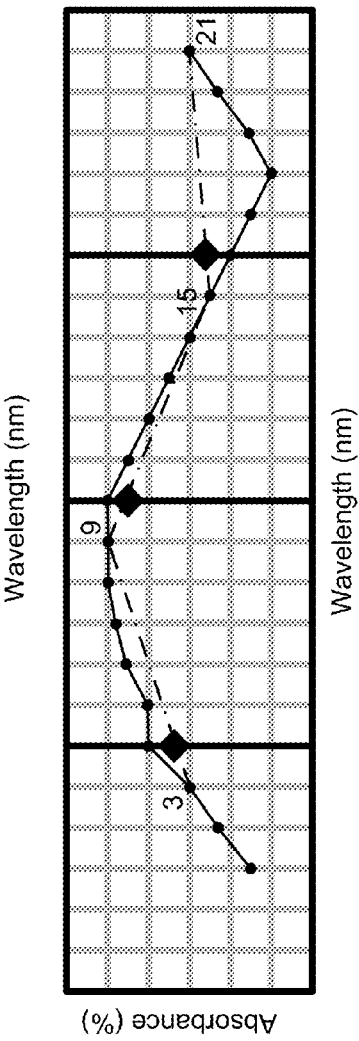

FIGS. 5A-5C are diagrams illustrating a manner in which modeling device 215 may perform shifted grid interpolation in order to augment the master calibration set. For the purposes of FIGS. 5A-5C, assume that modeling device 215 has received a master calibration set that, for a particular sample, includes a single high-resolution spectrum (e.g., generated based on spectral data collected during a single scan of the particular sample). The high-resolution of master instrument 205 is represented by the light gray grid lines in FIGS. 5A-5C, and the single spectrum is represented in FIGS. 5A-5C by a solid line including black dots at each measurable wavelength of the spectrum. The low-resolution of target instrument 210 is represented by the solid black squares in FIGS. 5A-5C. Here, the resolution of master instrument 205 is six times that of target instrument 210 in FIGS. 5A-5C.

As shown in FIG. 5A, modeling device 215 may generate a first replicate based on a first data point of the high-resolution spectrum, a seventh data point of the high-resolution spectrum, a thirteenth data point of the high-resolution spectrum, and a nineteenth data point of the high-resolution spectrum. As shown by the dashed line in FIG. 5A, these points may be connected and the first replicate may be formed based on points at which the connected data points intersect the low-resolution measureable wavelengths associated with target instrument 210 (i.e., where the dashed lines intersect the solid black squares). Here, the data points of the first replicate are shown as black diamonds in FIG. 5A.

As shown in FIG. 5B, modeling device 215 may generate a second replicate based on a second data point data point of the high-resolution spectrum, an eighth data point of the high-resolution spectrum, a fourteenth data point of the high-resolution spectrum, and a twentieth data point of the high-resolution spectrum. As shown by the dotted line in FIG. 5B, these points may be connected and the second replicate may be formed based on points at which the connected data points intersect the low-resolution measureable wavelengths associated with target instrument 210 (i.e., where the dotted lines intersect the solid black squares). Here, the data points of the second replicate are shown as black diamonds in FIG. 5B.

As shown in FIG. 5C, modeling device 215 may generate a third replicate based on a third data point of the high-resolution spectrum, a ninth data point of the high-resolution spectrum, a fifteenth data point of the high-resolution spectrum, and a twenty-first data point of the high-resolution spectrum. As shown by the dashed and dotted line in FIG. 5C, these points may be connected and the second replicate may be formed based on points at which the connected data points intersect the low-resolution measureable wavelengths associated with target instrument 210 (i.e., where the dashed and dotted lines intersect the solid black squares). Here, the data points of the third replicate are shown as black diamonds in FIG. 5C.

Notably, the resolution of the first replicate, the second replicate, and the third replicate match that of target instrument 210 (e.g., since every sixth data point was used to create the replicates). In this example, modeling device 215 has generated three low-resolution replicates from a single high-resolution scan. Here, modeling device 215 may augment the master calibration set by including the three replicates as spectra corresponding to the particular sample.

As indicated above, FIGS. 5A-5C are provided merely as examples associated with a shifted grid interpolation technique. Other examples are possible and may differ from what was described with regard to FIGS. 5A-5C. For example, in some implementations, modeling device 215 may generate additional replicates, fewer replicates, replicates with a different resolution, or the like, than those shown in FIGS. 5A-5C. In other words, FIGS. 5A-5C are provided merely as illustrative example of a manner in which modeling device 215 may perform shifted grid interpolation in order to augment the master calibration set. In some implementations, modeling device 215 may generate replicates, in order to augment the master calibration set, using a technique other than the shifted grid interpolation technique.

Returning to block 410 of FIG. 4, in some implementations, modeling device 215 may augment the master calibration set by generating replicates based on one or more spectra corresponding to one or more samples included in the master calibration set. For example, modeling device 215 may generate replicates for each sample for which a single spectrum is included in the master calibration set.

In some implementations, augmenting the master calibration set may lead to improved predictive accuracy of the transferred calibration model. For example, a root-mean-square error (RMSE) of a transferred calibration model, generated based on the augmented master calibration set, may be reduced as compared to a RMSE of a transferred calibration generated without augmentation of the master calibration set. Such improvement may be achieved when a transfer scheme is applied to a transfer set associated with generating the transferred calibration model, the details of which are described below. Similarly, such improvement may be achieved even when a transfer scheme is not applied to the transfer set.

In some implementations, augmentation of the master calibration set may allow a particular transfer scheme (e.g., a generalized least squares (GLS) scheme) to be applied to a transfer set created based on the augmented master calibration set. For example, in a case where the particular transfer scheme cannot be applied to a transfer set that includes a calibrant with single spectrum (i.e., when multiple spectra, associated with the calibrant, are needed to apply the transfer scheme), augmentation of the master calibration set allows the particular transfer scheme to be applied (e.g., since additional replicates are created via augmentation). Thus, improvements to the transferred calibration model that result from application of the particular transfer scheme may be realized despite the calibrant with the single spectrum being included in the master calibration set. Additional details regarding a transfer set, and the application of a transfer scheme to the transfer set, are described below.

As further shown in FIG. 4, process 400 may include selecting a set of master calibrants (block 415). For example, modeling device 215 may select a set of master calibrants. In some implementations, master instrument 205 may select the set of master calibrants after modeling device 215 creates the augmented master calibration set. Additionally, or alternatively, modeling device 215 may select the set of master calibrants after modeling device 215 obtains the master calibration set.

The selected set of master calibrants may include a set of spectra, corresponding to a set of samples included in the master calibration set, that is to be included in a transfer set associated with transferring the master calibration model from master instrument 205 to target instrument 210. In other words, spectra, corresponding to the selected set of master calibrants, may be used in association with transferring the master calibration model from master instrument 205 to target instrument 210. The transfer set may include the selected set of master calibrants and a corresponding selected set of target calibrants, and may be used to create a target calibration set based on the master calibration set. Additional details regarding the transfer set are described below.

In some implementations, the set of master calibrants may include a subset of the calibrants included in the augmented master calibration set. For example, the selected set of master calibrants may include spectra for four calibrants of 48 calibrants of the augmented master calibration set. Additionally, or alternatively, the set of master calibrants may include a subset of the calibrants included in the master calibration set (e.g., in a case where modeling device 215 does not augment a portion of the master calibration set).

Additionally, or alternatively, the set of master calibrants may include samples of a same type as those included in the augmented master calibration set. For example, in a case where a particular sample deteriorates over time, and modeling device 215 determines that the particular sample is to be included in the selected set of master calibrants, modeling device may identify a replacement sample, of the same type of the particular sample, for inclusion in the selected set of master calibrants.

In some implementations, modeling device 215 may select the set of master calibrants using a Kennard-Stone (KS) algorithm. The KS algorithm may cause modeling device 215 to select a set of master calibrants, of the augmented master calibration set, that provides uniform coverage of the master calibration set and that includes calibrants on the boundary of the augmented master calibration set.

In some implementations, modeling device 215 may apply the KS algorithm such that modeling device 215 selects the set of master calibrants based on a matrix of the calibration spectra included in the augmented master calibration set (i.e., based on multi-variate data with readings at different wavelengths). This approach may be referred to as KS-X selection.

Additionally, or alternatively, modeling device 215 may apply the KS algorithm such that modeling device 215 selects the set of master calibrants based on reference values (e.g., a measured amount of a compound) corresponding to the augmented master calibration set. This approach may be referred to as KS-Y selection.

Additionally, or alternatively, modeling device 215 may apply the KS algorithm such that modeling device 215 selects the set of master calibrants using both KS-X selection and KS-Y selection. In other words, modeling device 215 may use results of both KS-X selection and KS-Y selection in order to select the set of master calibrants. This approach may be referred to as KS-XY selection. As an example, assume that modeling device 215 is to select a set of five master calibrants. Here, when applying the KS-XY selection approach, modeling device 215 may select three master calibrants using the KS-X approach, and may select two master calibrants using the KS-Y selection approach.

In some implementations, selection of the set of master calibrants using a KS approach (e.g., KS-X selection, KS-Y selection, or KS-XY selection) may result in generation of a transferred calibration model that achieves improved performance as compared to a transferred calibration model generated based on a transfer set selected using a typical approach (e.g., a Leverage approach, a Leverage-Model Inverse approach, etc.). For example, a root-mean-square error of prediction (RMSEP) of a transferred calibration model, generated based on a transfer set including calibrants selected using a KS selection approach, may be reduced as compared to a transferred calibration model generated based on a transfer set including calibrants selected using a typical technique. As another example, a coefficient of determination ($R^2$) of the transferred calibration model, generated based on a transfer set including calibrants selected using a KS selection approach, may be increased as compared to the transferred calibration model generated based on a transfer set including calibrants selected using a typical technique.

In some implementations, modeling device 215 may select spectra for a small number of calibrants (e.g., two, three, five or fewer) for use in the transfer set. A transfer set including spectra associated with a small number of calibrants may be referred to as a sparse transfer set. In some implementations, use of a sparse transfer set to generate the transferred calibration model may reduce resource consumption of target instrument 210 and/or reduce a burden on a user of target instrument 210, as described in further detail below.

As further shown in FIG. 4, process 400 may include obtaining a selected set of target calibrants, associated with a target instrument, corresponding to the selected set of master calibrants (block 420). For example, modeling device 215 may obtain a selected set of target calibrants, associated with target instrument 210, corresponding to the selected set of master calibrants. In some implementations, modeling device 215 may obtain the selected set of target calibrants after modeling device 215 selects the set of master calibrants. Additionally, or alternatively, modeling device 215 may obtain the selected set of target calibrants when target instrument 210 provides the selected set of target calibrants.

The selected set of target calibrants may include a set of spectra, generated based on spectral data collected by target instrument 210, that corresponds to the samples associated with the selected set of master calibrants. In other words, the selected set of target calibrants may include spectra measured for a same set of samples (i.e., one or more same actual sample scanned by master instrument 205, one or more replacement samples of the same types as those scanned by master instrument 205, etc.) as the spectra included in the selected set of master calibrants. In some implementations, the selected set of target calibrants is to be included in a transfer set associated with transferring the master calibration model from master instrument 205 to target instrument 210. Additional details regarding the transfer set are described below.

In some implementations, a set of spectra, corresponding to a given sample associated with the selected set of target calibrants, may include one or more spectra. In some implementations, the spectra, included in the selected set of target calibrants, may be of a lower resolution than that of the spectra included in the master calibration set (e.g., since target instrument 210 may be a low-resolution device and master instrument 205 may be a high-resolution device).

In some implementations, modeling device 215 may obtain the selected set of target calibrants from target instrument 210. For example, modeling device 215 may select the set of master calibrants, as described above. Here, modeling device 215 may send, to target instrument 210, information that identifies the samples associated with the selected set of master calibrants (i.e., the samples for which spectra are included in the selected set of master calibrants). In this example, target instrument 210 may collect spectral data associated with the samples, and may generate and provide spectra, associated with the identified samples, to modeling device 215. Here, target instrument 210 may need to collect spectral data for only those samples associated with the selected set of master calibrants. In this way, resource usage and/or burden on a user may be reduced (e.g., since target instrument 210 need not generate spectra for every sample associated with the augmented master calibration set).

Additionally, or alternatively, modeling device 215 may obtain the selected set of target calibrants based on sending a request to target instrument 210 to provide the selected set of target calibrants. Additionally, or alternatively, modeling device 215 may obtain the selected set of target calibrants based on user input provided via target instrument 210 and/or modeling device 215.

As further shown in FIG. 4, process 400 may include creating a transfer set including the selected set of target calibrants and the selected set of master calibrants (block 425). For example, modeling device 215 may create a transfer set including the selected set of target calibrants and the selected set of master calibrants. In some implementations, modeling device 215 may create the transfer set after modeling device 215 receives the selected set of target calibrants.

The transfer set is a set of calibrants including the spectra associated with the selected set of target calibrants and the selected set of master calibrants. In some implementations, the transfer set may be used to generate a transfer matrix that is to be applied to the augmented master calibration set to create a target calibration set, as described below.

In some implementations, modeling device 215 may create the transfer set based on the selected set of target calibrants and the selected set of master calibrants. For example, modeling device 215 may create an association between one or more spectra, generated by target instrument 210 for a particular sample, and one or more spectra generated by master instrument 205 for the particular sample. In other words, for a given sample, modeling device 215 may match spectra, generated by target instrument 210, to spectra generated by master instrument 205. In some implementations, modeling device 215 may create such associations for each sample associated with the selected set of master calibrants in order to create the transfer set.

In some implementations, the transfer set may be a sparse transfer set, as described above. In other words, in some implementations, the transfer set may include spectra associated with a small number of samples (e.g., fewer than five). In some implementations, use of a sparse transfer set may reduce resource consumption of target instrument 210 and/or reduce burden on a user of target instrument 210 (e.g., since only a small number of scans are needed), without negatively impacting performance of the transferred calibration model.

Additionally, or alternatively, the transfer set may include a set of universal calibrants. The set of universal calibrants may include one or more calibrants that are application independent (e.g., where the calibrants included in the transfer set may typically include application specific calibrants, such as calibrants associated with identifying a pharmaceutical compound). For example, the set of universal calibrants may include a set of calibrants associated with a wavelength calibration standard, a set of calibrants associated with a photometric calibration standard, a set of calibrants that includes a combination calibrants associated with the wavelength calibration standard and the photometric calibration standard, or the like. In some implementations, the set of universal calibrants may be used to transfer a master calibration model, associated with a first application, to target instrument 210 associated with a second (i.e., different) application.

In some implementations, use of universal calibrants may reduce and/or eliminate resource usage and/or user burden associated with transferring the master calibration model to target instrument 210. For example, spectra, associated with the set of universal calibrants, may be generated as part of a manufacturing process of target instrument 210 (e.g., such that no spectral data needs to be collected at a later time in order to transfer the master calibration model to target instrument 210). In some implementations, the set of universal calibrants may be used alone (i.e., without the selected set of master calibrants and the selected set of target calibrants) to generate the transferred calibration model. Additionally, or alternatively, the set of universal calibrants may be used in addition to the selected set of master calibrants and the selected set of target calibrants.

As further shown in FIG. 4, process 400 may include generating a transfer matrix based on the transfer set (block 430). For example, modeling device 215 may generate a transfer matrix based on the transfer set. In some implementations, modeling device 215 may generate the transfer matrix after modeling device 215 creates the transfer set.

The transfer matrix may include a matrix, corresponding to the transfer set, associated with mapping the augmented master calibration set to generate a target calibration set from which the transferred calibration model may be generated. In other words, the transfer matrix may include information that identifies a manner in which the spectra, associated with the samples included in the master calibration set, may be manipulated in order to generate a target calibration set based on which the transferred calibration model may be created. In some implementations, modeling device 215 may create the transfer matrix based on the transfer set.

In some implementations, modeling device 215 may generate the transfer matrix after applying a transfer scheme to the transfer set. For example, modeling device 215 may apply a generalized least squares (GLS) scheme to the transfer set. The GLS scheme may function using the spectra included in the transfer set to estimate an offset and a shift in a covariance structure, associated with the spectral data, due to instrument differences. Here, the GLS scheme may remove variation in the spectral data, associated with the spectra included in the transfer set, that is not common to both master instrument 205 and target instrument 210. A result of applying GLS to the transfer set may be a transfer matrix that results in an improved transferred calibration model (e.g., as compared to a transfer matrix generated without application of a transfer scheme). In some implementations, modeling device 215 may apply another type of transfer scheme to the transfer set, such as a piecewise direct standardization (PDS) transfer scheme.

As further shown in FIG. 4, process 400 may include applying the transfer matrix to the augmented master calibration set to create a target calibration set (block 435). For example, modeling device 215 may apply the transfer matrix to the augmented master calibration set. In some implementations, modeling device 215 may apply the transfer matrix to the augmented master calibration set after modeling device 215 generates the transfer matrix.

The target calibration set may include sets of spectra, corresponding to the samples associated with the augmented master calibration set, from which the transferred calibration model may be generated. In other words, the target calibration set may include sets of spectra, associated with target instrument 210, that are mapped from sets of spectra corresponding to the samples included in the augmented master calibration set. Here, the sets of spectra included in the target calibration set may be mapped based on applying the transfer matrix to the sets of spectra included in the augmented master calibration set.

In some implementations, modeling device 215 may create the target calibration set based on applying the transfer matrix to the augmented master calibration set. For example, modeling device 215 may apply the transfer matrix to spectral data, associated with each sample included in the augmented master calibration set (i.e., spectral data associated with master instrument 205), where a result of applying the transfer matrix is spectral data to be associated with target instrument 210. In this way, spectral data for target instrument 210 may be obtained without a need for target instrument 210 to scan each sample associated with the augmented master calibration set. Rather, as described above, target instrument 210 need only collect spectral data for those samples associated with the sparse transfer set. In this way, the target calibration set may be obtained with a reduced consumption of target instrument 210 resources and/or user burden.

As further shown in FIG. 4, process 400 may include generating an optimized transferred calibration model, associated with the target instrument, based on the target calibration set (block 440). For example, modeling device 215 may generate the transferred calibration model, associated with target instrument 210, based on the target calibration set. In some implementations, modeling device 215 may generate the transferred model after modeling device 215 creates the target calibration set.

As described elsewhere herein, the transferred calibration model may include a model, to be used to calibrate measurements obtained by target instrument 210, that is generated based on a master calibration model associated with master instrument 205. In other words, the transferred calibration model may include a model that is transferred from master instrument 205 to target instrument 210, while accounting for differences between master instrument 205 and target instrument 210, such as resolution capability differences, hardware differences, optical path differences, or the like. In some implementations, modeling device 215 may optimized the generated calibration model using an optimization technique associated with the transfer set, as described below (i.e., modeling device 215 may generate an optimized transferred calibration model).

In some implementations, modeling device 215 may generate the transferred model based on applying a support vector regression (SVR) modeling technique (i.e., a support vector machine (SVM) for regression) to the target calibration set. The SVR modeling technique estimates coefficients of a regression equation, associated with the transferred calibration model, by minimizing a cost function. According to the SVR modeling technique, the cost function for building the transferred calibration model ignores values of spectral data, included in the transfer set, that are within a threshold of a prediction of the transferred calibration model (i.e., spectra of a sample with a cost that satisfies a threshold is ignored for purposes of generating the regression equation). Thus, the cost function, associated with the regression equation, is based on a subset of spectra included in the target calibration set (e.g., since spectral data associated with one or more samples may be ignored by the cost function). In some implementations, performance of a transferred calibration model generated using the SVR modeling technique is improved as compared to performance of a transferred calibration model generated using a typical modeling technique, such as a partial least squares (PLS) regression modeling technique.

In some implementations, modeling device 215 may generate the transferred calibration model using an optimization technique associated with optimizing the generated transferred calibration model. For example, in some implementations, modeling device 215 may determine a value of a model parameter (e.g., a C parameter associated with the SVR modeling technique, a PLS factor associated with the PLS regression modeling technique), associated with the transferred calibration model, based on the transfer set (e.g., the selected set of target calibrants, the selected set of master calibrants) that is selected using a KS selection approach (e.g., KS-X selection, KS-Y selection, KS-XY approach). Such a technique may be referred to as a XS-KS optimization technique.

Using the XS-KS optimization technique, modeling device 215 may determine the value of the model parameter of the master calibration model by running prediction on spectra, included in the transfer set, that are associated with target instrument 210. Here, the value of the model parameter that results in a RMSE that satisfies a threshold, or is a lowest RMSE, for the master calibration model may be identified as an optimal value of the model parameter, and the optimal value of the model parameter may be applied to the transferred calibration model associated with target instrument 210.

In some implementations, use of the XS-KS optimization technique to determine the value of the model parameter may result in improved model performance as compared to a typical technique for determining the value of the model parameter of transferred calibration model. For example, a typical manner of determining the value of the model parameter of the transferred calibration model uses a training set of spectra (i.e., associated with master instrument 205) to run cross validation in order to determine the value of the model parameter associated with the master calibration model. Here, the identified model parameter is applied to the transferred calibration model. However, using the training set of spectra to run cross validation in order to determine the value of the model parameter may not result in selection of an optimal model parameter (i.e., the model parameter, when applied to the transferred calibration model, may result in a higher RMSE as compared to one or more other possible values of the model parameter), thereby negatively impacting performance of the transferred calibration model. Here, use of the XS-KS optimization technique to determine the value of the model parameter may result in selection of a value of the model parameter that results in improved performance of the transferred calibration model, as compared to the value of the model parameter determined using the cross validation technique.

In some implementations, modeling device 215 may apply the XS-KS optimization technique to a transferred calibration model that is generated using the SVR modeling technique. Additionally, or alternatively, modeling device 215 may apply the XS-KS optimization technique to a transferred calibration that is generated using another modeling technique, such as the PLS regression modeling technique. For example, in the case of a transferred model that is generated using the PLS regression modeling technique, model performance may be improved by the XS-KS technique (e.g., as compared using the cross validation technique in conjunction with the PLS regression technique).

In some implementations, modeling device 215 may provide the transferred calibration model to target instrument 210. Here, target instrument 210 may receive and store the transferred calibration model such that target instrument 210 may calibrate measurements, collected by target instrument 210, at a later time using the transferred calibration model.

Although FIG. 4 shows example blocks of process 400, in some implementations, process 400 may include additional blocks, fewer blocks, different blocks, or differently arranged blocks than those depicted in FIG. 4. For example, in some implementations, modeling device 215 may not augment the master calibration set (i.e., block 410 may be optional). In such a case, other steps of process 400 may be performed based on the master calibration set (e.g., rather than the augmented master calibration set). Additionally, or alternatively, two or more of the blocks of process 400 may be performed in parallel.

Implementations described herein provide techniques for improved transfer of a master calibration model from a master instrument to a target instrument, while allowing the master calibration model to be transferred to the target instrument using a sparse transfer set that includes spectra associated with a small number of calibrants (e.g., five or fewer).

Notably, implementations described herein use a "forward" approach when transferring the master calibration model from master instrument 205 to target instrument 210. As described above, the master calibration set is mapped to target instrument 210 in order to obtain the target calibration set and generate the transferred calibration model. This approach differs from a typical calibration model transfer procedure, where target spectra, generated by a target instrument, is mapped to a master instrument, and the master calibration model is directly used to predict properties of a sample scanned the target instrument (a so-called "reverse" approach).

One advantage of using the forward approach is that this approach allows for periodic and/or continuous updating of the transferred calibration model. For example, one reason for performing a model transfer is to utilize an existing model developed on the master instrument such that the transferred model may be used by target instrument 210 for future measurements. Here, since such future measurements will be performed by target instrument 210, target instrument 210 may (e.g., in the future) collect additional spectral data that can be included in the transferred calibration model (e.g., in order to further improve or update the transferred calibration model, in order to make the transferred calibration model a better fit for a future condition, etc.). Use of the "forward" approach provides the flexibility to repeatedly update the transferred calibration model.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:
1. A device, comprising:
  a memory; and
  one or more processors to:
    obtain a master calibration set associated with a master calibration model of a master instrument,
      the master calibration set including spectra, associated with a set of samples, generated by the master instrument;
    identify a selected set of master calibrants based on the master calibration set, the selected set of master calibrants including spectra associated with a subset of the set of samples;
obtain a selected set of target calibrants associated with a target instrument,
the selected set of target calibrants including spectra, associated with the subset of the set of samples, generated by the target instrument;
create a transfer set based on the selected set of master calibrants and the selected set of target calibrants,
the transfer set being associated with the subset of the set of samples;
create a target calibration set, corresponding to the master calibration set, based on the transfer set; and
generate, based on a support vector regression modeling technique, a transferred calibration model, associated with the target instrument, based on the target calibration set,
the transferred calibration model being generated using an optimization technique associated with the transfer set.

2. The device of claim 1, where the select set of master calibrants is associated with five or fewer calibrants.

3. The device of claim 1, where the one or more processors are further to:
augment the master calibration set using a shifted grid interpolation technique to create an augmented master calibration set; and
where the one or more processors, when creating the target calibration set, are to:
create the target calibration set based on the augmented master calibration set.

4. The device of claim 1, where the one or more processors, when identifying the selected set of master calibrants, are to:
identify the selected set of master calibrants based on a Kennard-Stone (KS) selection approach.

5. The device of claim 1, where the one or more processors are further to:
determine a model parameter, associated with the transferred calibration model, using the selected set of target calibrants; and
where the one or more processors, when generating the transferred calibration model, are to:
generate the transferred calibration model based on the determined model parameter.

6. The device of claim 1, where the selected set of master calibrants is associated with a set of universal calibrants that are application independent.

7. The device of claim 1, where the one or more processors are further to:
generate a transfer matrix based on the transfer set; and
where the one or more processors, when creating the target calibration set, are to:
create the target calibration set by applying the transfer matrix to the master calibration set.

8. A non-transitory computer-readable medium storing instructions, the instructions comprising:
one or more instructions that, when executed by one or more processors, cause the one or more processors to:
obtain a master calibration set, associated with a master calibration model of a master instrument, that includes spectra associated with a set of samples,
the spectra being generated by the master instrument based on scanning the set of samples;
identify a selected set of master calibrants based on the master calibration set;
obtain a selected set of target calibrants, associated with a target instrument, corresponding to the selected set of master calibrants;
create a sparse transfer set based on the selected set of master calibrants and the selected set of target calibrants,
the sparse transfer set being associated with five or fewer samples of the set of samples;
generate a transfer matrix based on the sparse transfer set;
create a target calibration set, corresponding to the master calibration set, using the transfer matrix; and
generate a transferred calibration model, associated with the target instrument, based on the target calibration set,
the transferred calibration model being generated using an optimization technique associated with the sparse transfer set.

9. The non-transitory computer-readable medium of claim 8, where the one or more instructions, that cause the one or more processors to generate the transferred calibration model, cause the one or more processor to:
generate the transferred calibration model using a support vector regression modeling technique.

10. The non-transitory computer-readable medium of claim 8, where the one or more instructions, when executed by the one or more processors, further cause the one or more processors to:
augment the master calibration set to create an augmented master calibration set; and
where the one or more instructions, that cause the one or more processors to create the target calibration set, cause the one or more processors to:
create the target calibration set based on applying the transfer matrix to the augmented master calibration set.

11. The non-transitory computer-readable medium of claim 8, where the one or more instructions, that cause the one or more processors to identify the selected set of master calibrants, cause the one or more processors to:
identify the selected set of master calibrants based on a Kennard-Stone (KS) selection approach.

12. The non-transitory computer-readable medium of claim 8, where the one or more instructions, when executed by the one or more processors, further cause the one or more processors to:
determine a model parameter, associated with the transferred calibration model, using the selected set of target calibrants; and
where the one or more instructions, that cause the one or more processors to generate the transferred calibration model, cause the one or more processors to:
generate the transferred calibration model based on the determined model parameter.

13. The non-transitory computer-readable medium of claim 8, where the master calibration set is associated with a set of universal calibrants.

14. The non-transitory computer-readable medium of claim 8, where the one or more instructions, when executed by the one or more processors, further cause the one or more processors to:
apply a transfer scheme to the sparse transfer set; and
where the one or more instructions, that cause the one or more processors to generate the transfer matrix, cause the one or more processors to:
generate the transfer matrix after applying the transfer scheme to the sparse transfer set.

15. A method, comprising:
obtaining, by a device, a first calibration set associated with a first calibration model of a first instrument,
 the first calibration set including spectra, associated with a set of samples, generated based on scans of the set of samples by the first instrument;
identifying, by the device, a first selected set of calibrants of the first calibration set,
 the first selected set of calibrants corresponding to a subset of the set of samples that includes five or fewer samples;
obtaining, by the device, a second selected set of calibrants associated with a second instrument,
 the second selected set of calibrants including spectra, associated with the subset of the set of samples, generated based on scans of the subset of the set of samples by the second instrument;
creating, by the device, a transfer set based on the first selected set of calibrants and the second selected set of calibrants,
 the transfer set corresponding to the subset of the set of samples;
creating, by the device, a second calibration set, corresponding to the first calibration set, based on the transfer set; and
generating, by the device and based on the second calibration set, a second calibration model associated with the second instrument,
 the second calibration model being generated based on a support vector regression modeling technique, and
 the second calibration model being generated using an optimization technique associated with the transfer set.

16. The method of claim 15, further comprising:
providing the second calibration model to the second instrument.

17. The method of claim 15, further comprising:
augmenting the first calibration set, using a shifted grid interpolation technique, to create an augmented first calibration set; and
where creating the second calibration set comprises:
 creating the second calibration set based on the augmented first calibration set.

18. The method of claim 15, where identifying the first selected set of calibrants comprises:
identifying the first selected set of calibrants based on a Kennard-Stone (KS) selection approach.

19. The method of claim 15, further comprising:
determining a model parameter, associated with the second calibration model, based on the transfer set; and
where generating the second calibration model comprises:
 generating the second calibration model based on the determined model parameter.

20. The method of claim 15, where the first selected set of calibrants and the second selected set of calibrants are associated with a set of application independent calibrants.

* * * * *